United States Patent
Stark (10) Patent No.: US 7,456,407 B2
(45) Date of Patent: Nov. 25, 2008

(54) SYSTEM FOR MEDICAL IMAGING AND A PATIENT SUPPORT SYSTEM FOR MEDICAL DIAGNOSIS

(75) Inventor: Iain Stark, Manotick (CA)

(73) Assignee: IS2 Medical Systems Inc., Nepean, Ontario (CA)

( * ) Notice: Subject to any disclaimer, the term of this patent is extended or adjusted under 35 U.S.C. 154(b) by 303 days.

(21) Appl. No.: 10/959,547

(22) Filed: Oct. 6, 2004

(65) Prior Publication Data

US 2005/0211905 A1    Sep. 29, 2005

(30) Foreign Application Priority Data

Mar. 19, 2004    (CA) .................................. 2461964

(51) Int. Cl.
*G01T 1/166* (2006.01)
(52) U.S. Cl. ............................. 250/363.08; 250/363.05
(58) Field of Classification Search ............ 250/363.08, 250/363.02, 363.04, 363.05; 378/15
See application file for complete search history.

(56) References Cited

U.S. PATENT DOCUMENTS

| | | | |
|---|---|---|---|
| 5,034,970 A | 7/1991 | Yahata et al. | |
| 5,059,799 A * | 10/1991 | Kurakake | 250/363.1 |
| 5,554,848 A * | 9/1996 | Hermony et al. | 250/363.05 |
| 5,717,212 A * | 2/1998 | Fulton et al. | 250/363.05 |
| 5,966,422 A | 10/1999 | Dafni et al. | |
| 6,373,060 B1 * | 4/2002 | Yamakawa et al. | 250/363.08 |
| 6,617,582 B2 | 9/2003 | Stark | |
| 6,966,422 B2 | 11/2005 | Lanfranchi | |
| 2003/0163015 A1 | 8/2003 | Yanagisawa et al. | |
| 2007/0069137 A1 * | 3/2007 | Campbell et al. | 250/363.02 |

FOREIGN PATENT DOCUMENTS

EP    1 005 257 A2    5/2000

* cited by examiner

*Primary Examiner*—Christine Sung
*Assistant Examiner*—Faye Boosalis
(74) *Attorney, Agent, or Firm*—Pearne & Gordon LLP (57) ABSTRACT

A system for medical imaging and a patient support system for medical diagnosis are provided. The system includes a gantry mounted on the base. The gantry has an annular support. A detector head is fixed to the inner surface of the annular support. The annular support rotates along an axis of the inner space, and is prevented from moving in horizontal and vertical direction and moving angularly. The patient support system has a patient bed system having a plurality of configurations. The contact surface of the patient has a couch back support, a thigh support and a leg support. A controller is provided for angular movements of the supports, and for vertical/horizontal movements of the supports.

14 Claims, 15 Drawing Sheets

SYSTEM FOR MEDICAL IMAGING AND A PATIENT SUPPORT SYSTEM FOR MEDICAL DIAGNOSIS

FIELD OF THE INVENTION

The present invention relates to a medical system, more specifically, to a system for medical imaging and a patient support system for medical diagnosis.

BACKGROUND OF THE INVENTION

Scintillation cameras are well known in the art of nuclear medicine, and are used for medical diagnostics. A patient ingests, inhales or is injected with a small quantity of a radioactive isotope. The radioactive isotope emits radiations that are detected by a scintillation medium in the scintillation camera. The scintillation medium is commonly a sodium iodide crystal, BGO or other. The scintillation medium emits a small flash or scintillation of light in response to stimulating radiation from a patient. The intensity of the scintillation light is proportional to the energy of the stimulating radiation, such as a gamma ray.

A conventional system for a scintillation camera such as a gamma camera includes a detector head, which detects gamma rays emitted from a patient and converts them into electrical signals and a processor for processing the signals output from the detector. The detector head includes a scintillator and an array of photomultiplier tubes. The gamma rays are directed to the scintillator, which absorbs the radiation and produces a very small flash of light. The array of photodetectors, which are placed in optical communication with the scintillation crystal, convert these flashes into electrical signals which are subsequently processed. The processor processes the signals output from the array to produce an image of the distribution of the radioisotope within the patient.

For obtaining desired images, improvement has been performed in this field. For example, a patient is placed on a flat bed, while a gamma camera(s) is rotated around a gantry and is further moved towards and away from the axis of rotation. Additional mechanical components may be added to angle the gamma camera.

While such systems have improved the quality of the images, complicated arrangements are required to position the detector head and the bed needs a full length of a human body to support a patient. That affects the size of the system. Additionally, a patient may feel uncomfortable since he or she must keep his/her posture straight. Further, it is difficult to obtain supine and prone imagines in systems that have limited rotation of 180° and operate one the principle of raising and lowering the detector on a vertical column.

It is, therefore, desirable to provide a new system with compact size, and can easily position a patient with respect to a medical device, and can make the patient comfortable.

SUMMARY OF THE INVENTION

It is an object of the present invention to provide a system, which obviates or mitigates at least one of the disadvantages described above.

In accordance with an aspect of the present invention, there is provided a system for medical imaging includes: a base; a gantry mounted on the base, the gantry having an annular support ring, which defines a cylindrical inner space, and a detector head for a nuclear camera, which is fixed to the inner surface of the annular supporting; a mechanism for allowing the annular support ring to rotate along a centre axis of the inner space and for preventing horizontal, vertical and angular movements of the annular support; and a bed system for supporting and adjustably positioning a patient at a location with respect to the detector head.

In accordance with a further aspect of the present invention, there is provided a system for supporting and positioning a patient for medical diagnosis, includes: (1) a contact surface for the patient including a couch back support having a first end and a second end, a thigh support having a first end pivotably connected to the second end of the couch back support, and a second end, and a leg support having a first end pivotably connected to the second end of the thigh support, and a second end; (2) a link mechanism for pivotably linking the couch back support, the thigh support and the leg support; and (3) a control system for providing angular movements to the couch back support, the thigh support and the leg support.

A further understanding of other features, aspects and advantages of the present invention will be realized by reference to the following description, appended claims, and accompanying drawings.

BRIEF DESCRIPTION OF THE DRAWINGS

The invention will be further understood from the following description with reference to the drawings in which.

DETAILED DESCRIPTION OF THE PREFERRED EMBODIMENT(S)

Figure 1:
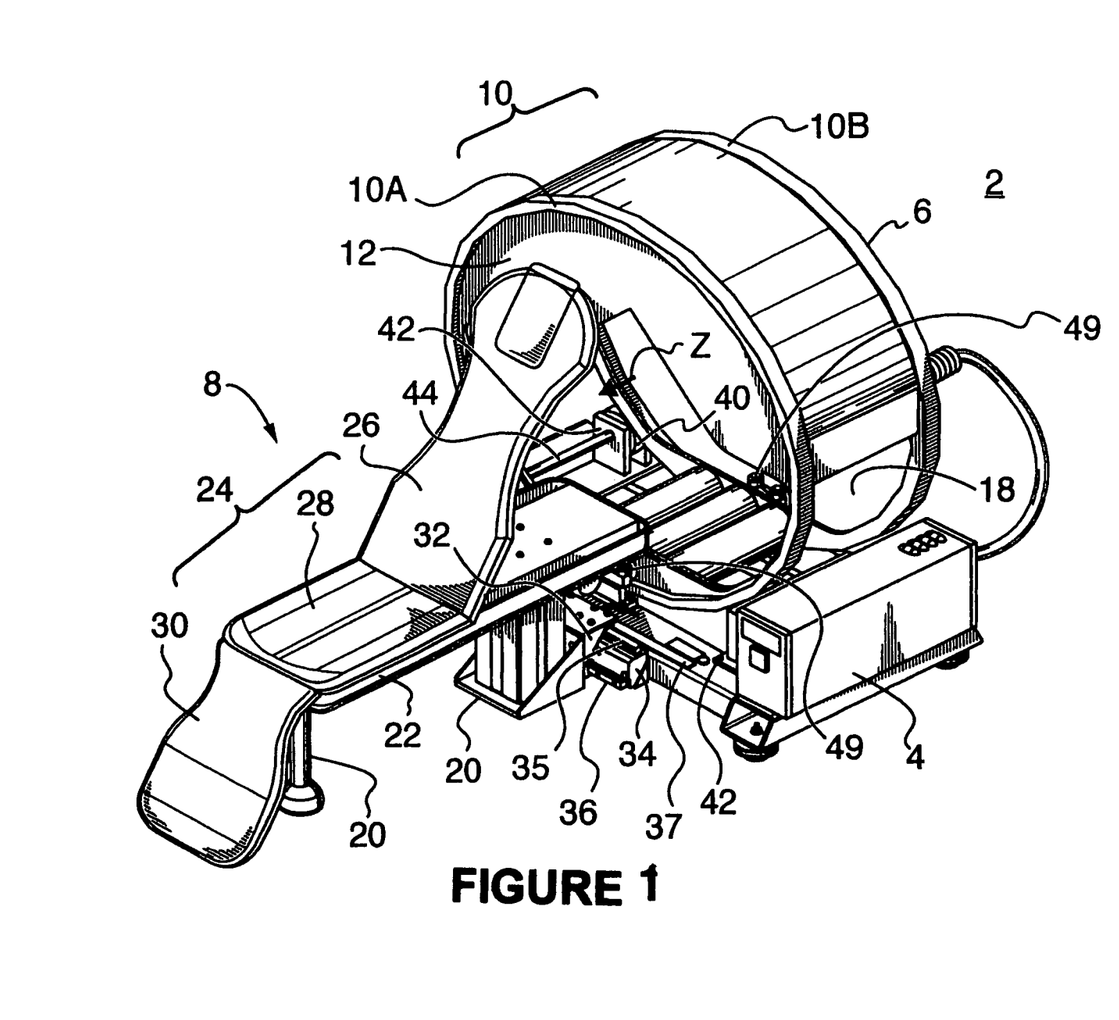
FIG. 1 is a perspective view showing a medical diagnosis system in accordance with an embodiment of the invention.

FIG. 1 shows a medical diagnosis system 2 in accordance with an embodiment of the present invention. The medical diagnosis system 2 includes a base 4, a gantry 6 for a medical nuclear camera and a patient bed system 8 for supporting and positioning a patient. The gantry 6 is mounted on the base 4 and has an annular support 10. The annular support 10 supports and guides a detector head 12 for the nuclear camera. The nuclear camera may be a scintillation camera or gamma camera, and may be a Cardiac Gamma Camera.

The base 4 has a fixing mechanism for fixing the base 4 on a flat plane (e.g. floor or wall) and a moving mechanism for moving the base 4 on the plane.

The annular support 10 has an inner surface (14 of FIG. 2) and an outer surface (16 of FIG. 2), and defines a cylindrical inner space 18. The detector head 12 is fixed to the inner surface (14) of the annular support 10 so as to be positioned within the cylindrical inner space 18. A mechanism for rotating the annular support 10 is provided. This mechanism allows the annular support 10 to rotate along the center axis Z of the inner space 18, and prevents the annular support 10 from moving in a direction horizontal to the axis Z and in a direction vertical to the axis Z, and sliding and sloping about the axis Z. In FIG. 1, the annular support 10 includes a pair of annular rings 10A and 10B disposed parallel to each other.

The patient bed system 8 has a support base 20, a horizontal plane 22 on the base 20 and a patient support system 24. The patient support system 24 includes a couch back support 26, a thigh support 28 and a leg support 30. The patient support system 24 has a plurality of configurations as described below. Such configurations may be done by automatic control and/or manual control.

The patient bed system 8 is detachably attached to the base 4 through a connector element 32 located at the support base 20, which engages with a connector element 34 located at the base 4. The patient bed system 8 can move laterally with respect to the base on rails 35 and 36. An actuator 37 provides a controlled and reproduceable later motive power.

Figure 2:
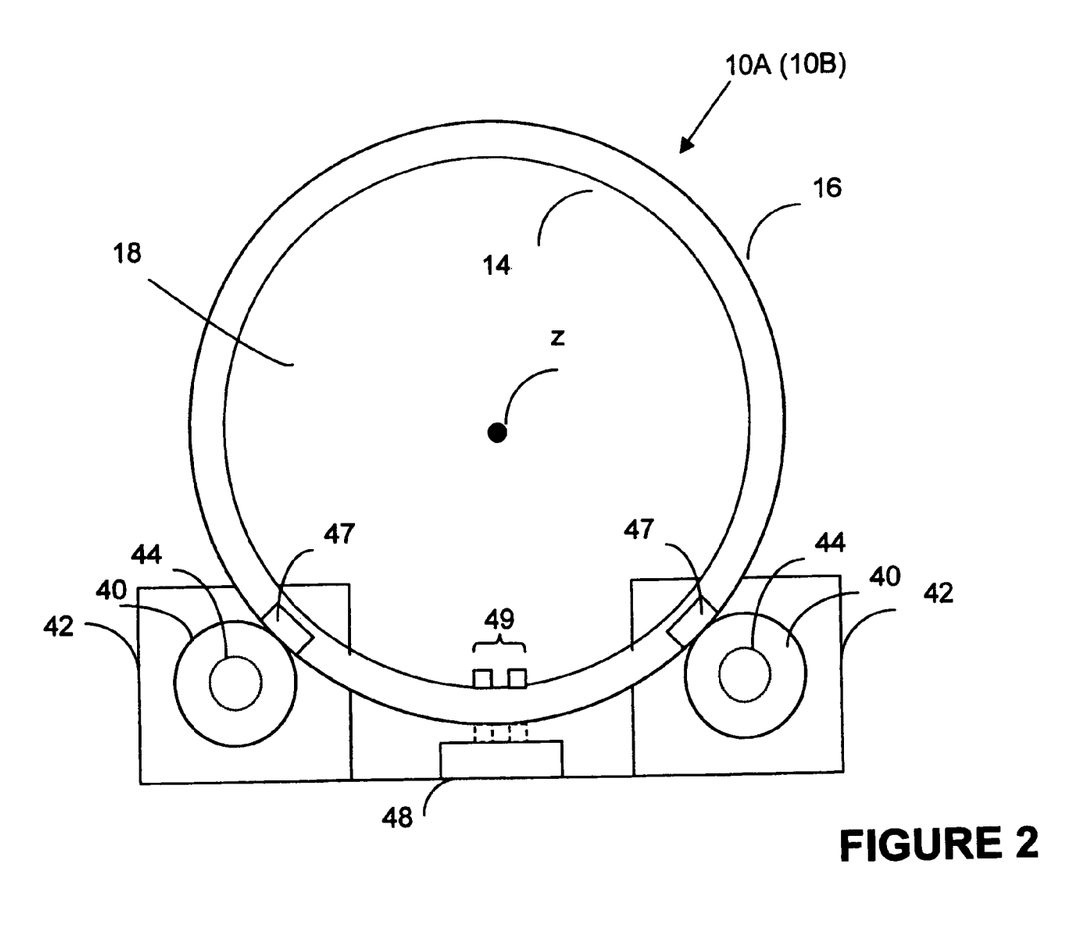
FIG. 2 is a diagram showing an example of the rotation mechanism provided to the annular support of FIG. 1.

The rotation mechanism of the annular support 10 of FIG. 1 is described in detail. FIG. 2 is an example of the rotation mechanism provided to the annular support 10. In FIG. 2, "14" represents the inner surface of the annular support 10 and "16" represents the outer surface of the annular support 10.

A roller 40 is provided to each side of the annular support ring 10A (10B). The roller 40 is rotatably mounted on a brace 42 fixed to the base 4. The roller 40 located at one side of the support ring 10A is connected to the roller located at the same side of the annular support ring 10B through a rod 44. The roller 40 engages with the outer surface 16 of the annular support 10 such that the annular support 10 is rotated by the roller 40. A drive unit (46 of FIG. 11) is provided to at least one roller 40 such that power is transferred from the drive unit to the roller 40. Cam followers 47 mounted on the brace 42 locate the annular support ring 10A in horizontal direction. Rings 49 mounted on the brace 48 ensure that the angular support rings 10A cannot become detached from the rollers 40.

Figure 3:
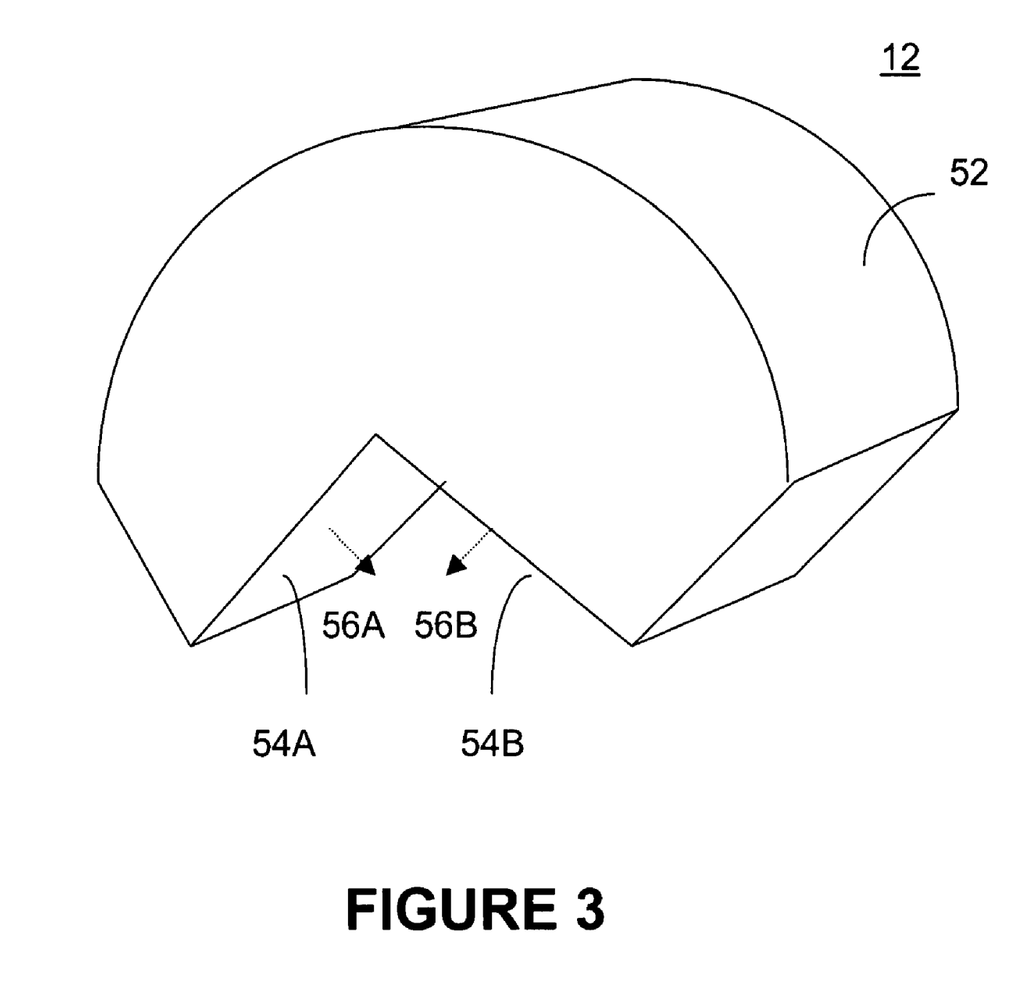
FIG. 3 is a diagram showing a housing of the detector head of FIG. 1.

One embodiment of the detector head 12 of FIG. 1 is described in details. FIG. 3 shows the housing 52 of the detector head 12. The detector head 12 has two scintillation detectors disposed in the V-shaped housing 52. The housing 52 is rigidly fixed to the inner surface 14 of the annular support 10. The housing 52 has two planes 54A, 54B, which are connected to each other at substantially 90 degrees. Each detector has an array of photo multipliertubes, a collimator plate and a scintillation crystal located on the corresponding plane. The collimator holes or channels extend to the surface of the surface of the corresponding collimator plate. The structure and components of the detector head 12 are, for example, disclosed on U.S. Pat. No. 6,617,582, which is incorporated herewith by reference.

The collimator plate for one detector is angled at substantially 90 degrees to the other detector, which prevents stray radiation from entering the collimator. This eliminates the requirement for lead shielding the detection field 56A and 56B of the detectors. Thus, the detection field 56A and 56B can be closer together, which minimizes risk of cutting off views during the operation.

One embodiment of the patient support system 24 of FIG. 1 is described in details. The patient support system 24 adjusts a patient position and/or a patient posture as described below.

Figure 4:
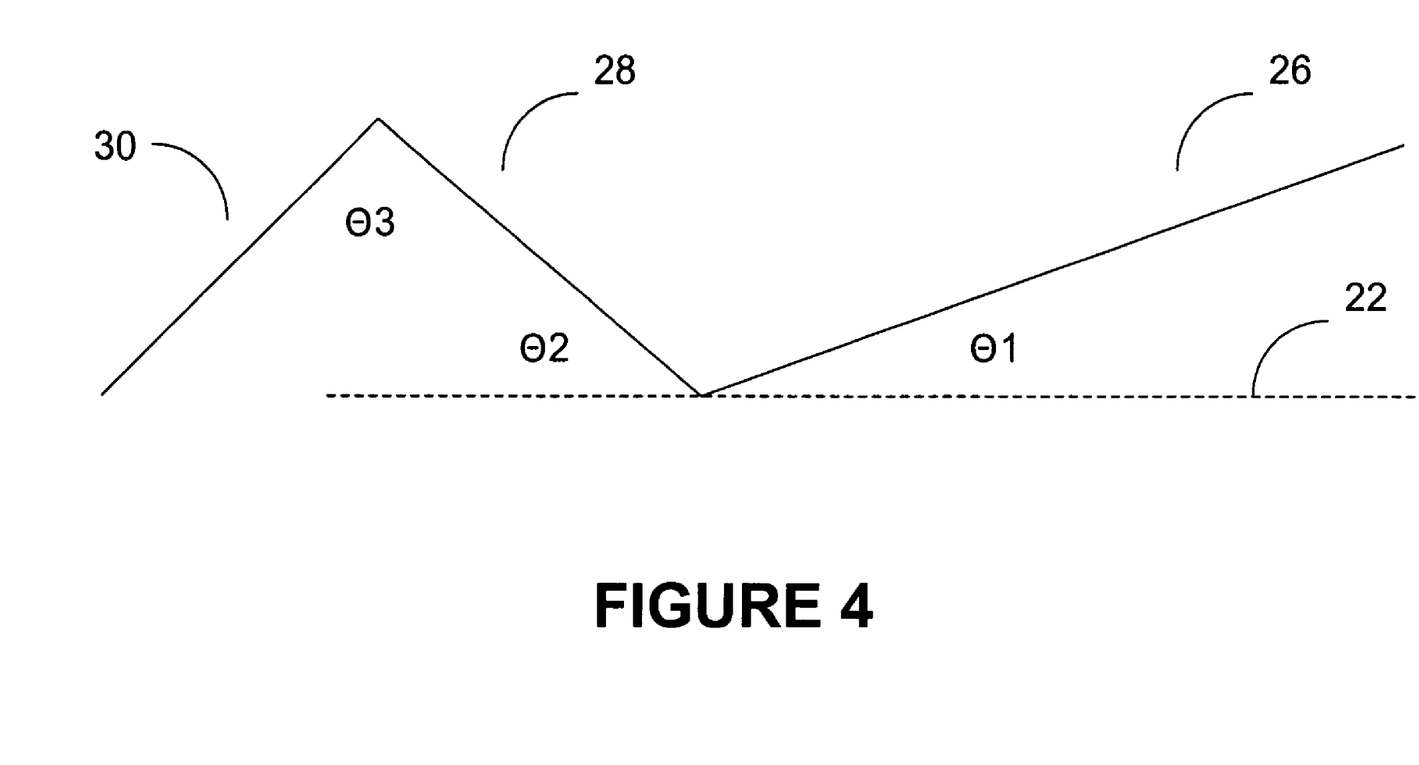
FIG. 4 is a schematic side view showing the patient support system of FIG. 1.

FIG. 4 shows the relationship among the couch back support 26, the thigh support 28 and the leg support 30 of FIG. 1. "$\Theta 1$," represents an angle between the couch back support 26 and the horizontal plane 22. "$\Theta 2$" represents an angle between the thigh support 28 and the horizontal plane 22. "$\Theta 3$" represents an angle between the thigh support 28 and the leg support 30. The angles $\Theta 1$, $\Theta 2$, $\Theta 3$ are adjusted as described below.

Figure 5:
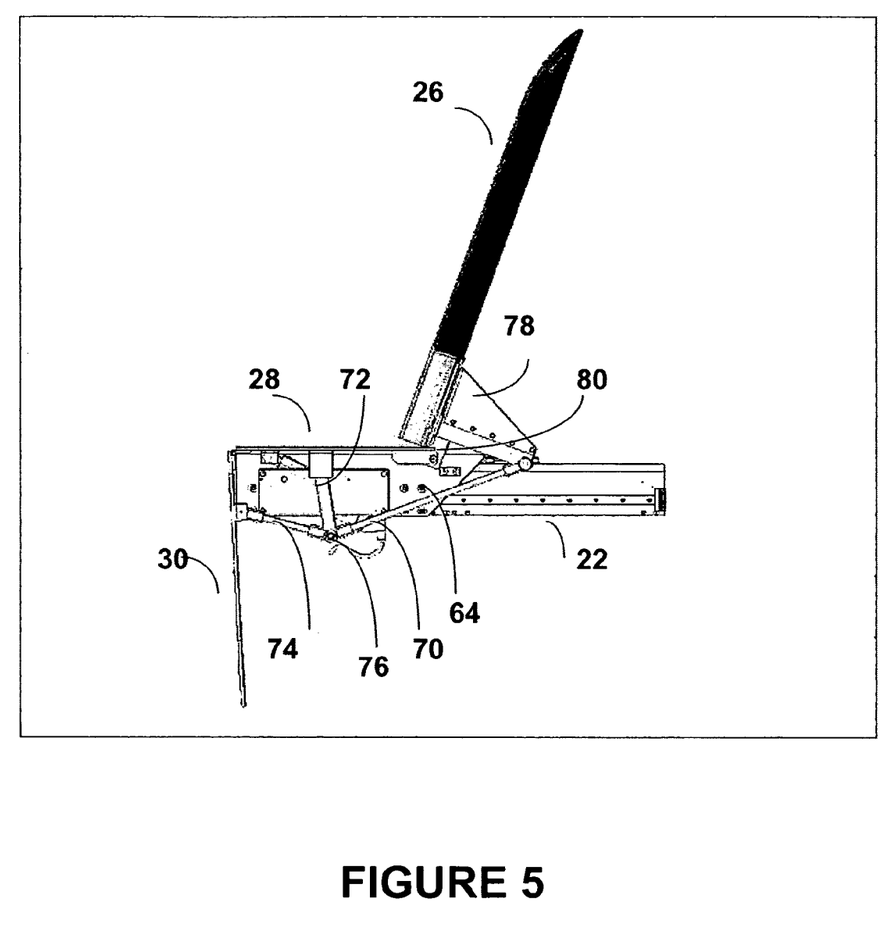
FIG. 5 is a side view showing an example of a configuration of the patient support system.
Figure 6:
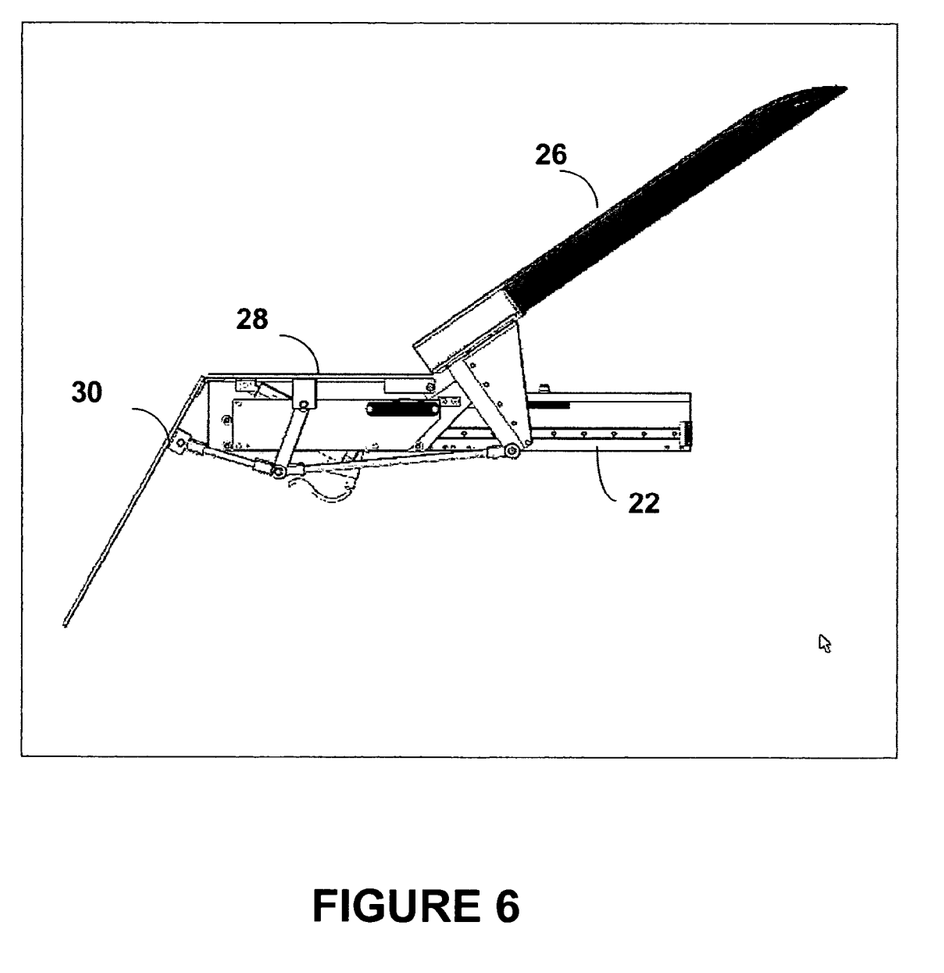
FIG. 6 is a side view showing further example of the configuration of the patient support system.
Figure 7:
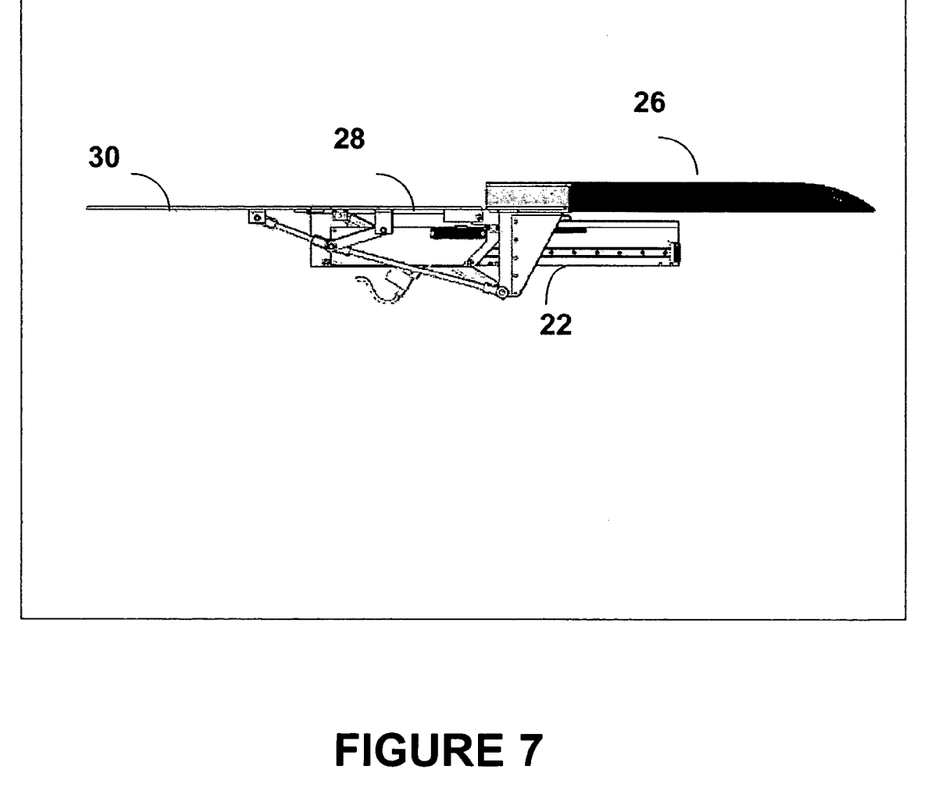
FIG. 7 is a side view showing further example of the configuration of the patient support system.
Figure 8:
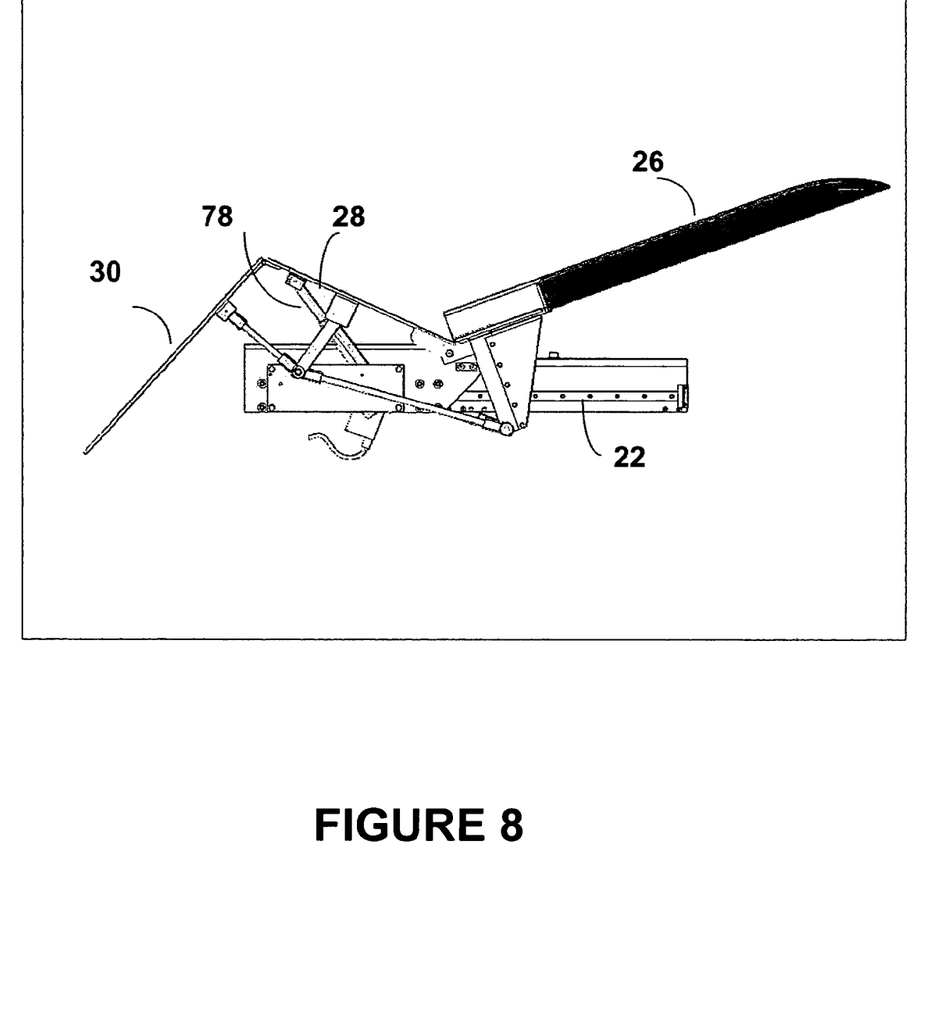
FIG. 8 is a side view showing further example of the configuration of the patient support system.
Figure 9:
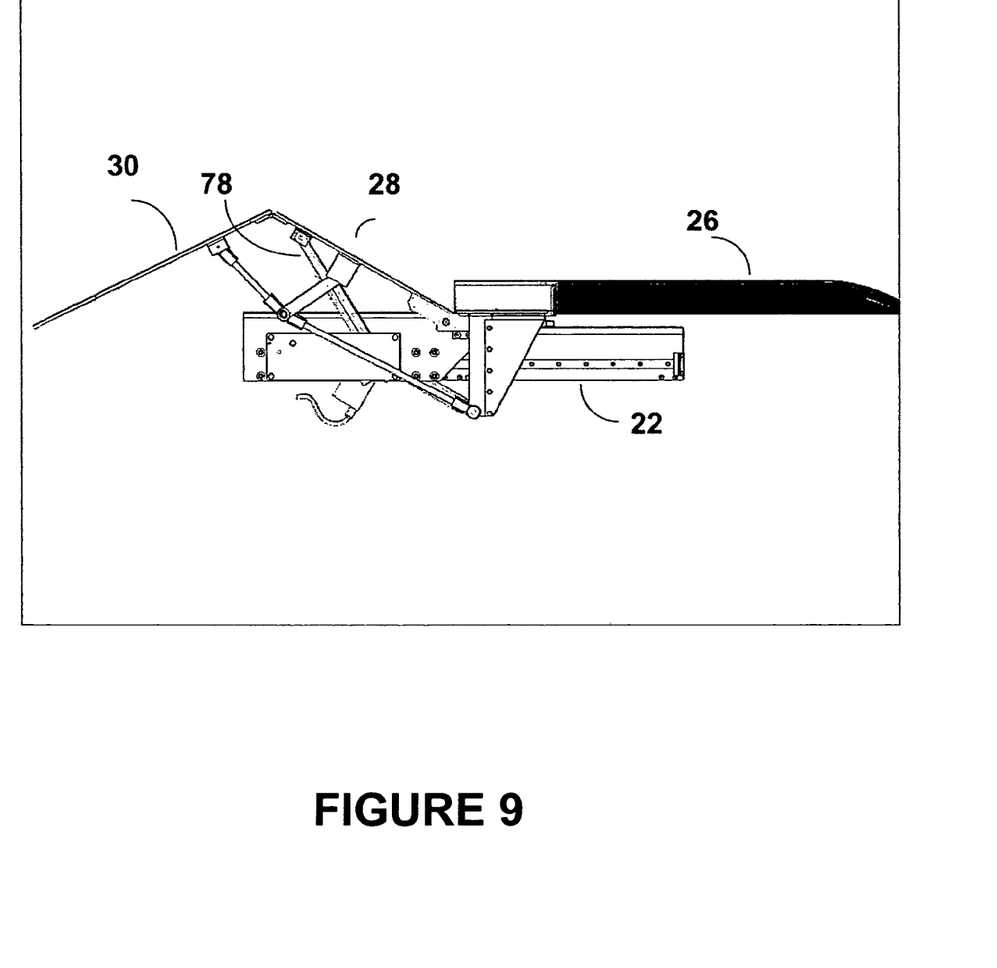
FIG. 9 is a side view showing further example of the configuration of the patient support system.
Figure 10:
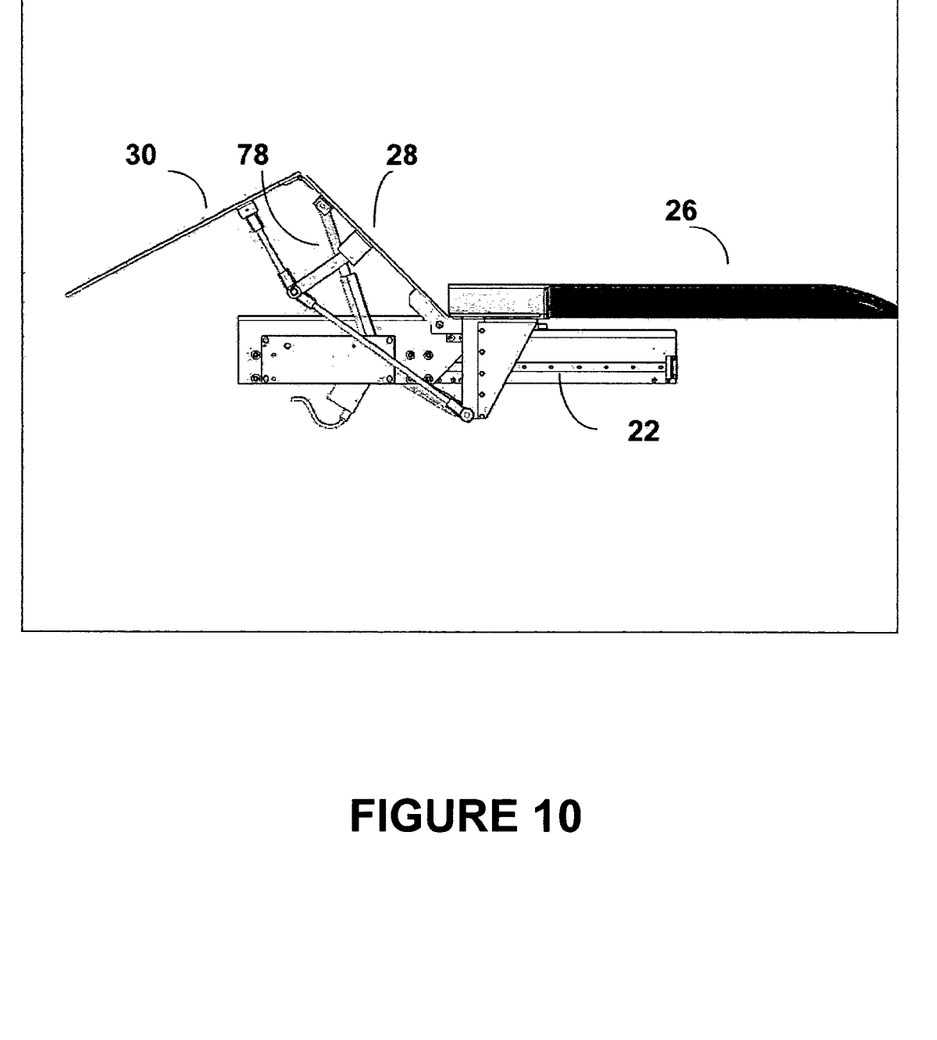
FIG. 10 is a side view showing further example of the configuration of the patient support system.

FIGS. 5-10 show examples of the configurations of the patient support system 24. In FIG. 5, the patient support system 24 forms a chair. In FIG. 6, the couch back support 26 and the leg support 30 are angled against the plane 22. In FIG. 7, the patient support system 24 forms a flat bed. In FIGS. 8-10, the thigh support 28 is angled upwardly against the plane 22.

The couch back support 26, the thigh support 28 and the leg support 30 are linked together through a set of link arms 70, 72 and 74. One end of the link arm 70 is pivotably connected to the couch back support 26 through a plate 78, and the other end is pivotably connected to a connection element 76. One end of the link arm 72 is pivotably connected to the thigh support 28, and the other end is pivotably connected to the connection element 76. One end of the link arm 74 is pivotably connected to the leg support 30, and the other end is pivotably connected to the connection element 76. The similar set of link arms may be provided to the other side of the supports 26-30.

One end of the thigh support 28 and one end of the couch back support 26 are pivotably connected to a sliding table 64 at a connection point 80. The sliding table 64 horizontally slides on the plane 22. The other end of the thigh support 28 and one end of the leg support is pivotably connected to each other.

The patient support system 24 may have one or more than one actuator to adjust the angles $\Theta 1$-$\Theta 3$. As shown in Figures, the patient support system 24 may further include an adjustable arm 78, which is connected to the thigh support 28, to change its length under the control of the actuator. The thigh support 28 is angled when the adjustable arm 78 changes its length and puts the thigh support 28 upwardly.

The patient support system 24 can be converted in a plurality of different ways. For example, the patient for supine may be placed on the support system 24 of FIG. 5. Then, the support system 24 may be converted to that of FIG. 6. Further, the support system 24 of FIG. 6 may be converted to that of FIG. 7.

Referring to FIGS. 5 and 8-10, another example for converting the patient support system 24 is described in detail. At first, the angles $\Theta 1$ and $\Theta 2$ are set to 70° and 0°, respectively (FIG. 5). A patient is mounted on the patient support system 24. Then, the couch back support 26 is angled backwardly through a first actuator (108 of FIG. 11). The angle $\Theta 1$ is decreased at $\Theta 1 = x°$ (<70°). "x" may be adjusted by settings of relative actuator speeds.

When $\Theta 1$ reaches the specific value x, a second actuator (110 of FIG. 11) is powered. The thigh support 28 is angled upwardly through the second actuator. The angle $\Theta 2$ is increased. The couch back support 26 is further angled backwardly such that the head of the patient moves downwardly. The leg support 30 is raised upwardly (FIG. 8).

Finally, the angle Θ1 is 0, and the couch back support 26 is in its flat position (FIG. 9). The angle Θ2 is set to a specific value, which is large enough so that the leg support 30 clears a trough. For example, Θ2 is set to 32°, while the angle Θ3 is 108°. The leg support 30 may be raised higher as required on a per patient basis (FIG. 10).

The data Θ1-Θ3 may be pre-calculated for each patient based on his/her physical and/or medical information.

Figure 11:
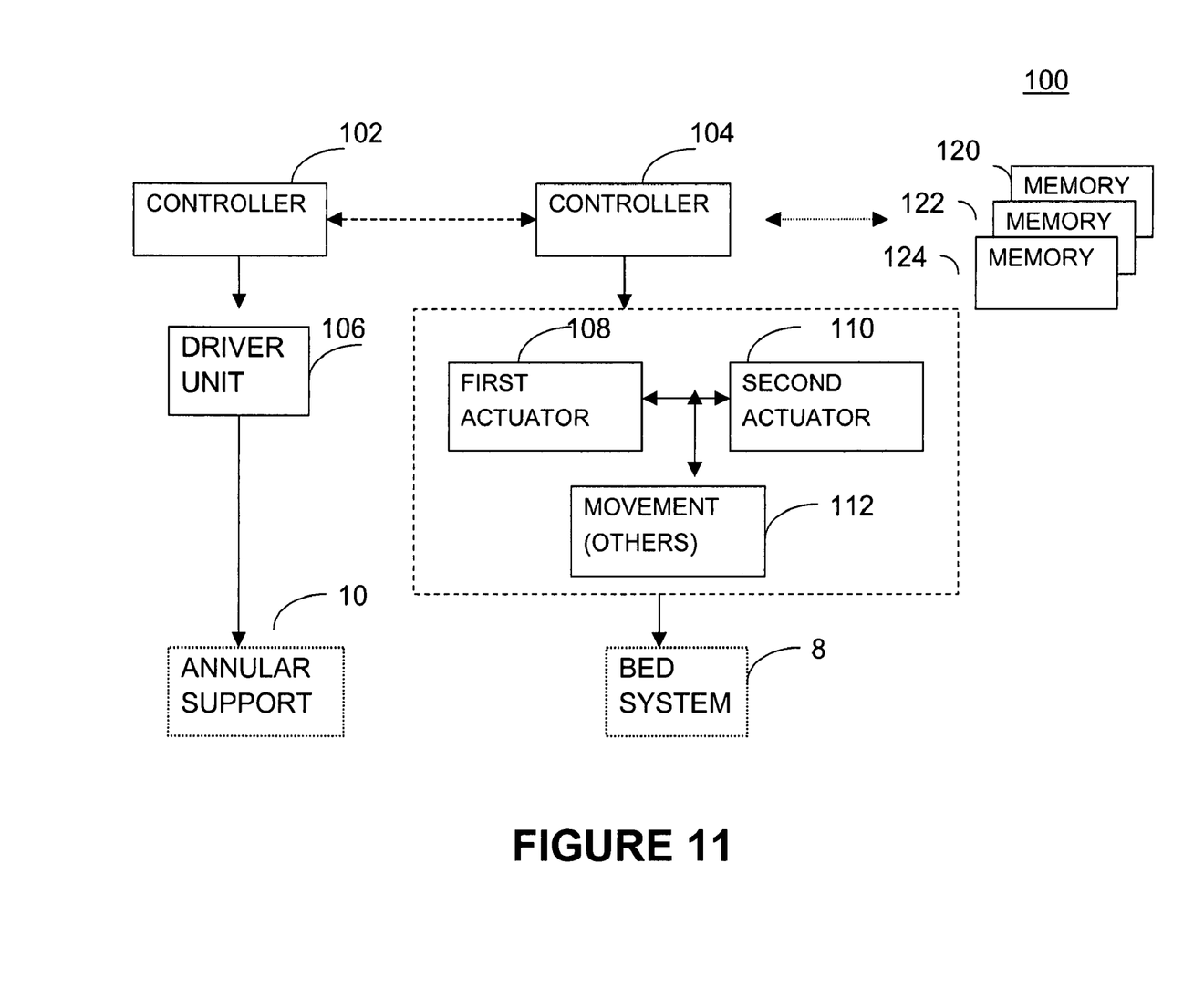
FIG. 11 is a block diagram showing a control. system for the medical diagnosis system of FIG. 1.

FIG. 11 is a diagram showing a control system 100 for the medical diagnosing system 2 of FIG. 1. The control system 100 may be located on the base 4. The control system 100 includes a controller 102 for the annular support 10, and a controller 104 for the patient bed system 8. The controller 104 controls an actuator (e.g., 108, 110, or 108 and 110) for setting the patient support system 24 as described above. In FIG. 11, the actuators 108 and 110 are shown. However, only one actuator may be provided to the patient support system 24. The controller 104 may control the patient bed system 8 in cooperation with the controller 102 as described below.

Figure 12:
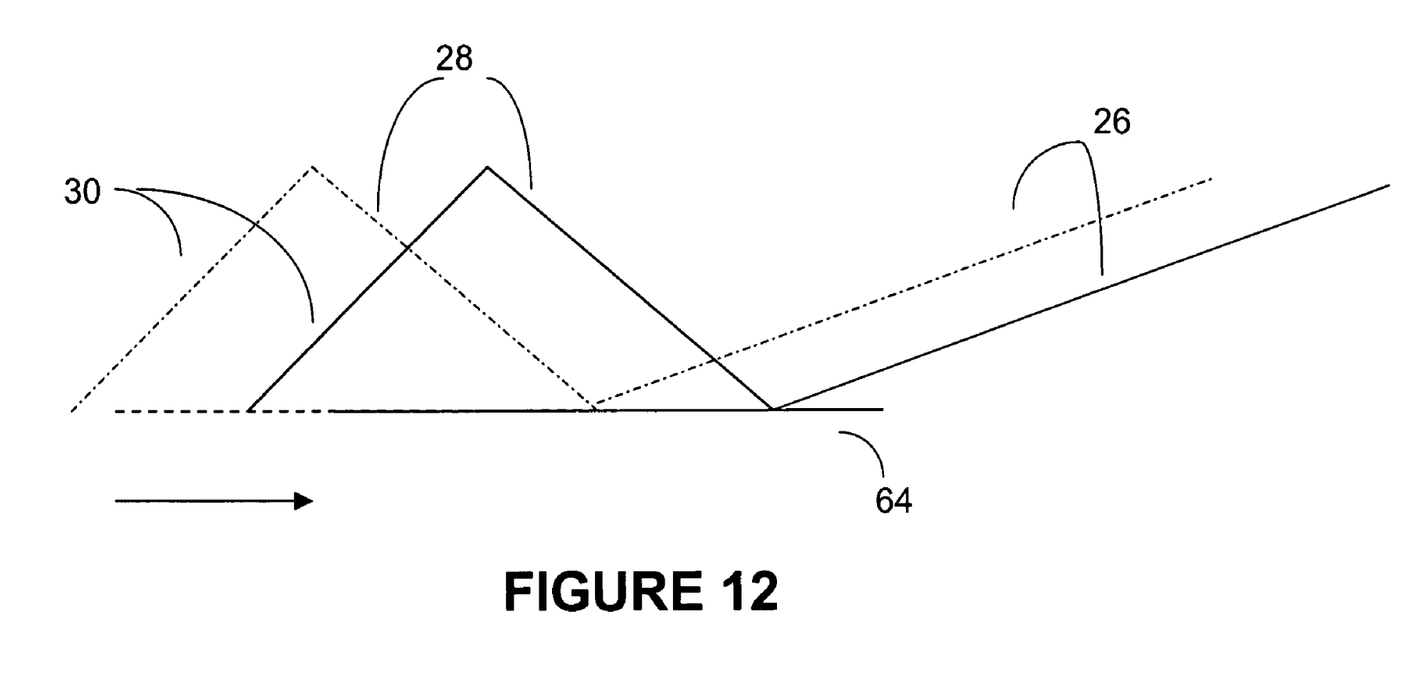
FIG. 12 is a diagram showing the horizontal movement of the patient support system.
Figure 13:
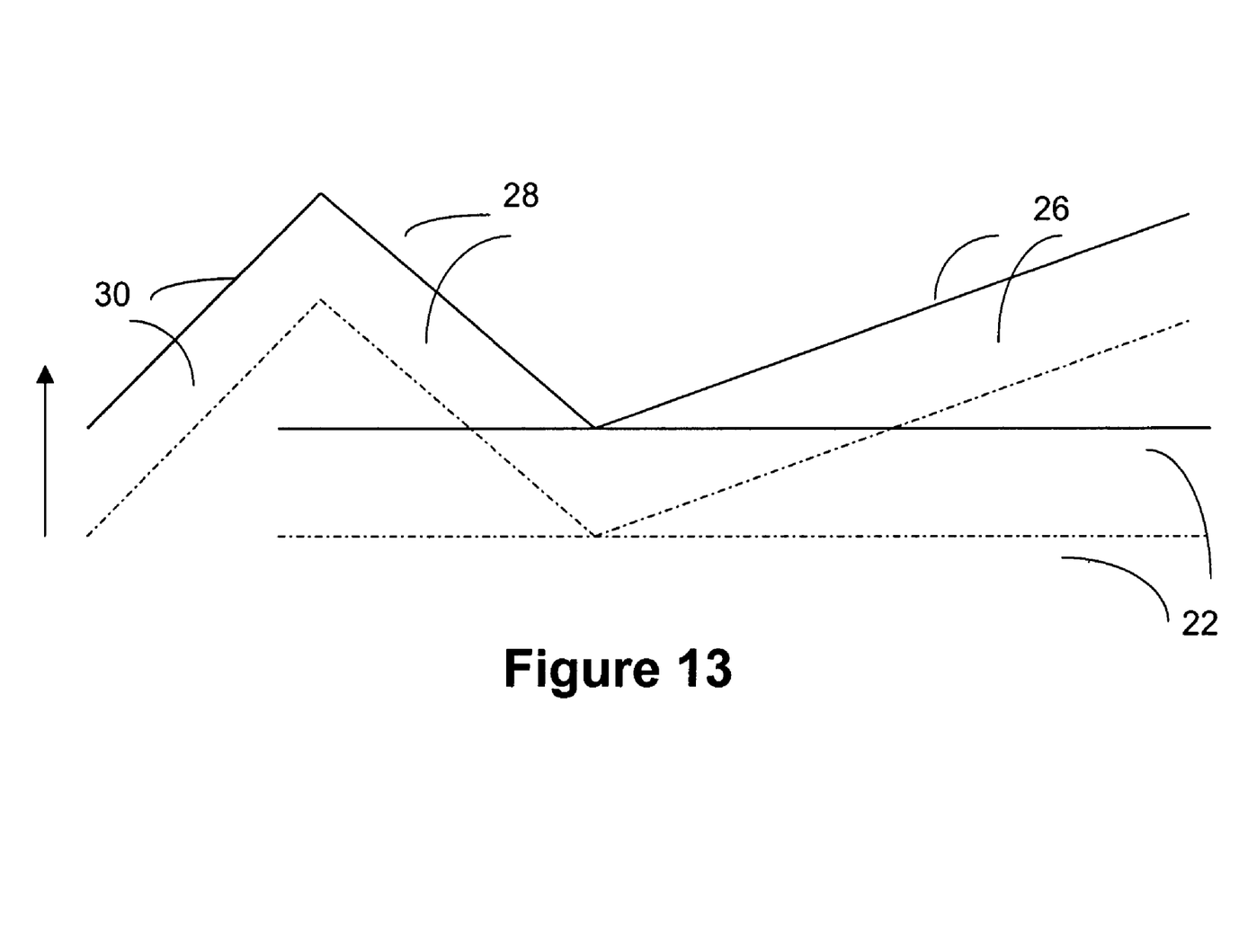
FIG. 13 is a diagram showing the vertical movement of the patient support system.

The controller 104 controls the mechanism 112 for horizontally moving the sliding table (64 of FIG. 5) on the patient support system 24 (as shown in FIG. 12) and for vertically moving the horizontal plane 22 (as shown in FIG. 13). This mechanism 112 allows the position of a patient to be vertically and horizontally adjusted.

The control system 100 further includes an image memory 120 for storing projection images obtained by the detector head 12, a program memory 122 for image processing, and a memory 124 for storing information on a patient. The memory 124 stores, for example, patient's prone/supine information. When starting the operation of the medical diagnosis system 2, the patient may be suitable positioned based on the information pre-stored on the memory 124.

An output device (e.g. a display, a printer) and an input/control device (e.g. a keyboard, a mouse, a track ball) may be provided to the control system 100, and may be detachably connected to the base 4.

Figure 14:
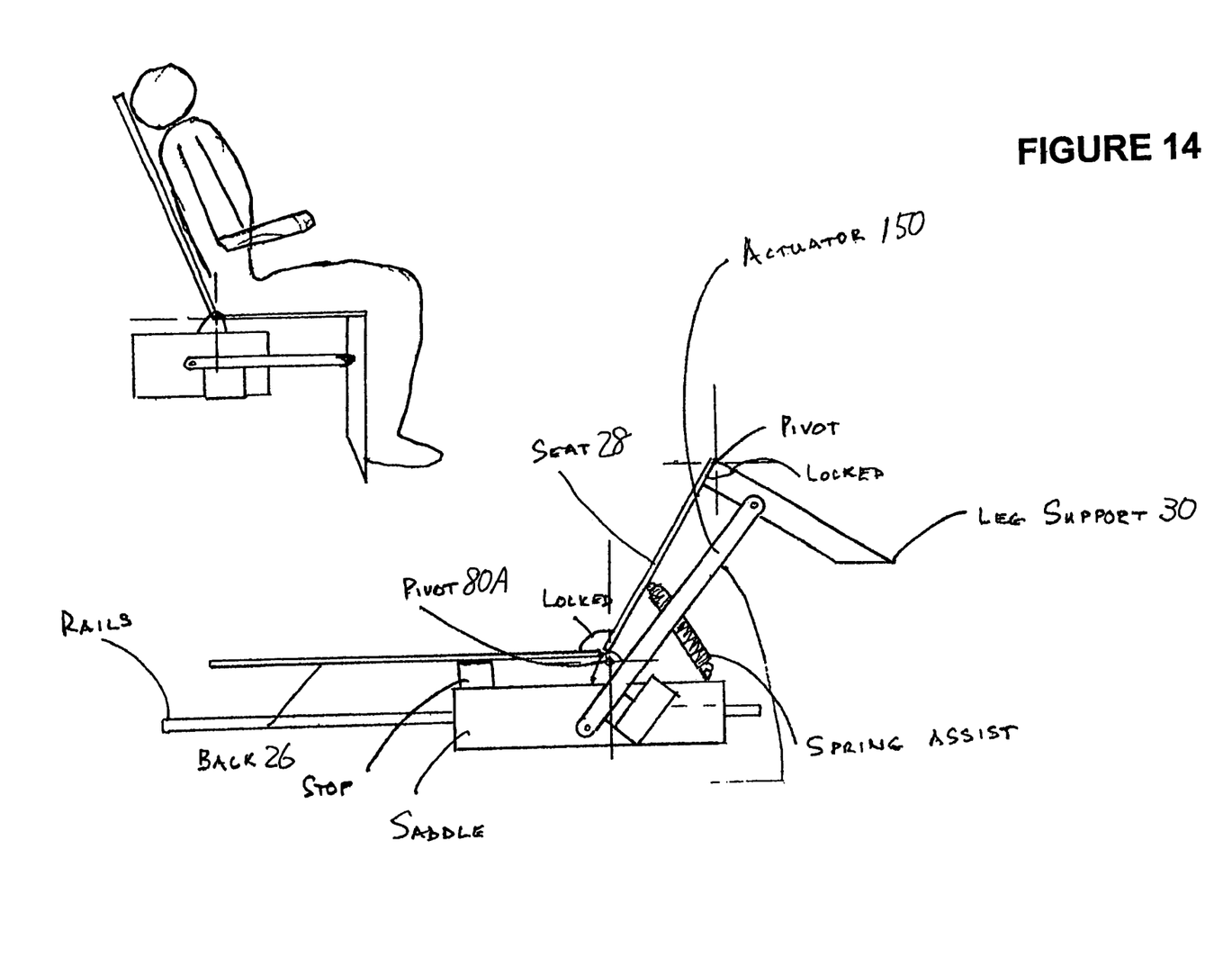
FIG. 14 is a side view showing another embodiment of the patient support system that is applied to the system of FIG. 1.
Figure 15:
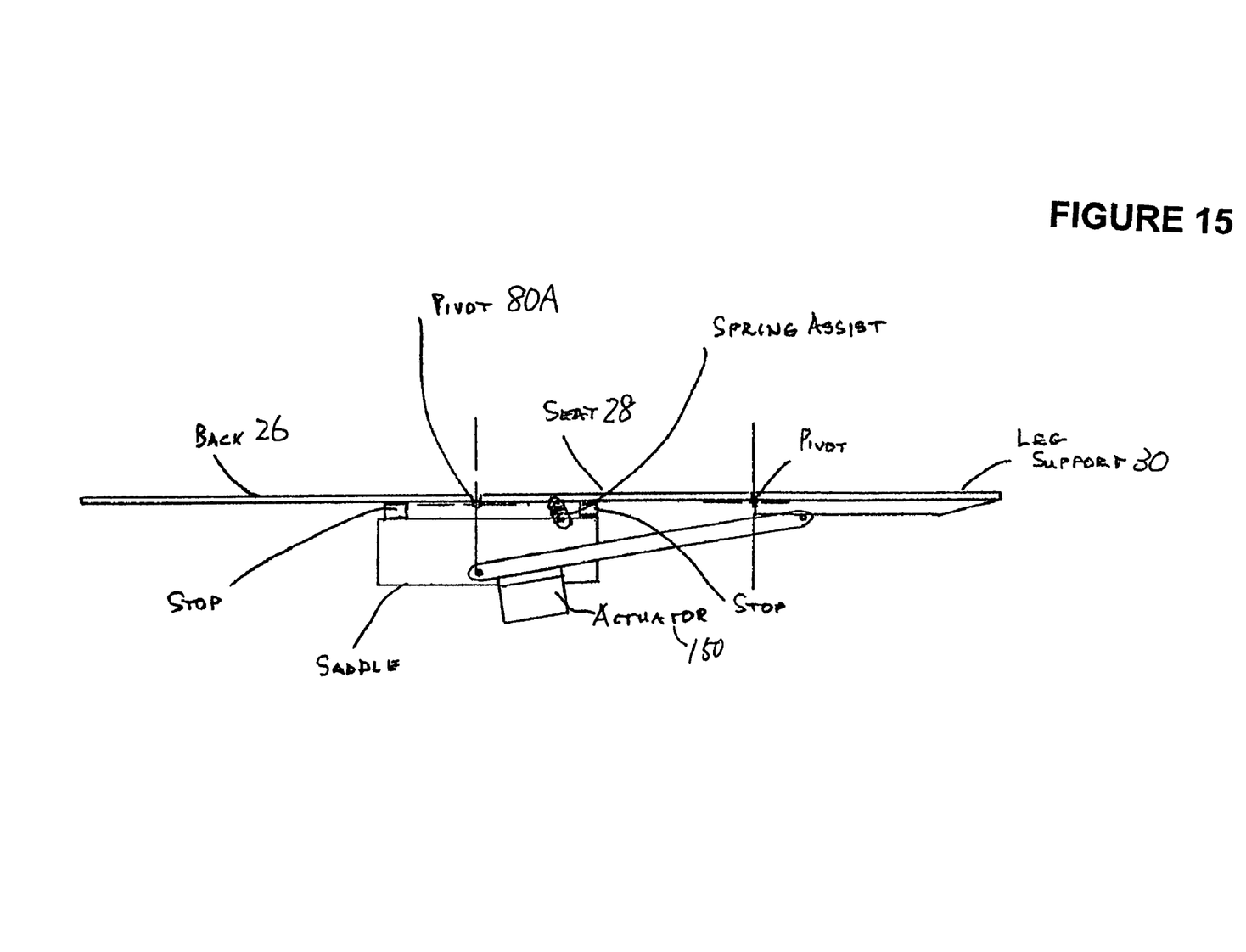
FIG. 15 is a side view showing further example of the configuration of FIG. 14.

FIGS. 14 and 15 show another embodiment of the patient support system 24. In FIGS. 14 and 15, one actuator 150 is used to adjust the bed/seat of the patient support system 24.

When the actuator 150 pulls and the seat 28 and back 26 are locked at the angle shown in FIG. 14, then the whole seat will lift the patient into an upright position as shown above. When the actuator 150 pushed the patient is laid down for imaging.

When the locks are released, the actuator 150 extended the bed/seat straightens out as shown in FIG. 15. The seat/leg support pivot 80A cannot exceed 180°. The stops assume a flat bed position.

According to the embodiment of the present invention, the system uses a mechanism that allows the detector head to rotate within the inner space of the gantry and enables the system to obtain desired images without moving up/down or tilting the detector head.

According to the embodiment of the present invention, the detector head 12 is located inside the gantry 6. Thus, the floor space for placing the system is reduced. As the movement of the detector head 12 is limited, complicated structural arrangements are not required comparing to the conventional systems. Further, the patient bed system 8 is detachably attached to the base 4. Thus, the gantry 6 with the detector head 12 and the patient bed system 8 can be moved separately from each other.

According to the embodiment of the present invention, a patient can be placed at a desired position with respect to the detector head. It allows full range of nuclear medicine studies, and allows the system to obtain supine and prone images. Furthermore, the position of the patient is adjustable to comfort the patient.

While particular embodiments of the present invention have been shown and described, changes and modifications may be made to such embodiments without departing from the scope of the invention.

What is claimed is:

1. A system for medical imaging comprising:
   a gantry including:
      an annular support ring having an inner surface and an outer surface, said inner surface defining a cylindrical inner space, and
      a detector head having one or more detectors for nuclear radiation detection and a housing for said one or more detectors, said housing being fixed to said inner surface of said annular support ring so that said one or more detectors are fixed at a predetermined distance from said annular support ring, and
   a mechanism for allowing said annular support ring to rotate along a centre axis of said inner space and for preventing horizontal, vertical and angular movements of said annular support ring,
      said mechanism including:
         one or more braces being fixed to a base;
         one or more rollers for said one or more braces, each rotatably mounted on the corresponding brace and engaging with said outer surface of said annular support ring for rotating said annular support ring; and
         a device mounted on at least one of said one or more braces for locating said annular support ring in a predetermined direction.

2. The system as claimed in claim 1, wherein the mechanism includes a drive unit located on said base for generating rotation movement, and a transfer element for transferring said rotation movement to said annular support ring.

3. The system as claimed in claim 1, wherein said one or more detectors include a pair of detectors, and wherein said housing is a V-shaped housing for said pair of detectors.

4. The system as claimed in claim 3, wherein said pair of said detectors are disposed at substantially 90 degrees to each other.

5. The system as claimed in claim 1, further comprising a bed system for a patient, and wherein said bed system is detachably attached to said base.

6. The system as claimed in claim 1, further comprising a supporting system for supporting and adjustably positioning a patient at a location with respect to said detector head.

7. The system as claimed in claim 6, wherein the supporting system includes a contact surface of said patient and a mechanism for changing the configuration of said contact surface.

8. The system as claimed in claim 7, wherein the configuration includes a flat bed surface and a chair.

9. The system as claimed in claim 7, further comprising a mechanism for moving said contact surface at least in vertical and horizontal directions.

10. The system as claimed in claim 1, wherein the base comprises a moving mechanism for moving the based on a plane.

11. The system as claimed in claim 1, wherein said one or more braces include a pair of braces for sides of said annular support ring, said one or more rollers including a pair of rollers for said sides of said annular support ring.

12. The system as claimed in claim 11, wherein said device is mounted on each of the braces for locating said annular support ring in a horizontal direction.

13. The system as claimed in claim 11, wherein the mechanism comprises:
   a device for preventing detachment of said annular support ring from said pair of rollers.

14. A system for medical imaging comprising:
   a gantry including:
      an annular support ring having an inner surface and an outer surface, said inner surface defining a cylindrical inner space, and
      a detector head having one or more detectors for nuclear radiation detection and a housing for said one or more detectors, said housing being fixed to said inner surface of said annular support ring so that said one or more detectors are fixed at a predetermined distance from said annular support ring, and
   a mechanism for allowing said annular support ring to rotate along a centre axis of said inner space and for preventing horizontal, vertical and angular movements of said annular support ring,
   wherein said mechanism comprises:
      a pair of braces for sides of said annular support ring, said braces being fixed to a base;
      a pair of rollers for said sides of said annular support ring, each rotatably mounted on the corresponding brace and engaging with said outer surface of said annular support ring for rotating said annular support ring; and
      a device mounted on the brace for locating said annular support ring in a horizontal direction.

* * * * *